(12) United States Patent
Mao et al.

(10) Patent No.: US 12,161,409 B2
(45) Date of Patent: Dec. 10, 2024

(54) APPARATUS AND METHOD FOR IMAGING STRUCTURE IN A TRANSPARENT MEDIUM

(71) Applicants: Topcon Corporation, Tokyo (JP); National University Corporation Tokyo Medical and Dental University, Tokyo (JP)

(72) Inventors: Zaixing Mao, Tokyo (JP); Kyoko Ohno-Matsui, Tokyo (JP); Hiroyuki Takahashi, Tokyo (JP); Noriko Nakao, Tokyo (JP)

(73) Assignees: TOPCON CORPORATION, Tokyo (JP); NATIONAL UNIVERSITY CORPORATION TOKYO MEDICAL AND DENTAL UNIVERSITY, Tokyo (JP)

(*) Notice: Subject to any disclaimer, the term of this patent is extended or adjusted under 35 U.S.C. 154(b) by 484 days.

(21) Appl. No.: 17/669,388

(22) Filed: Feb. 11, 2022

(65) Prior Publication Data

US 2022/0313075 A1    Oct. 6, 2022

Related U.S. Application Data

(60) Provisional application No. 63/168,927, filed on Mar. 31, 2021.

(51) Int. Cl.
*A61B 3/00* (2006.01)
*A61B 3/10* (2006.01)
(Continued)

(52) U.S. Cl.
CPC ............ *A61B 3/0025* (2013.01); *A61B 3/102* (2013.01); *G06T 7/0012* (2013.01); *G06T 7/11* (2017.01);
(Continued)

(58) Field of Classification Search
CPC ..... A61B 3/0025; A61B 3/102; G06T 7/0012; G06T 7/11; G06T 11/008; G06T 2200/04;
(Continued)

(56) References Cited

U.S. PATENT DOCUMENTS

2014/0152957 A1* 6/2014 Reisman ............... G06T 7/0012
351/246
2020/0279352 A1    9/2020 Mao et al.

OTHER PUBLICATIONS

Sebag, "Imaging Vitreous", Eye, 2002, vol. 16, No. 4, pp. 429-439.
(Continued)

*Primary Examiner* — James C. Jones
(74) *Attorney, Agent, or Firm* — XSENSUS LLP

(57) ABSTRACT

A medical diagnostic apparatus includes a receiver circuit that receives three-dimensional data of an eye, and processing circuitry configured to segment the three-dimensional data into regions that include a target structural element and regions that do not include the target structural element to produce a segmented three-dimensional data set. The segmenting is performed using a plurality of segmentation algorithms. Each of the plurality of segmentation algorithms is trained separately on different two-dimensional data extracted from the three-dimensional data. The processing circuitry is further configured to generate at least one metric from the segmented three-dimensional data set, and evaluate a medical condition based on the at least one metric.

20 Claims, 8 Drawing Sheets

(51) Int. Cl.
G06T 7/00 (2017.01)
G06T 7/11 (2017.01)
G06T 11/00 (2006.01)

(52) U.S. Cl.
CPC ........ G06T 11/008 (2013.01); G06T 2200/04 (2013.01); G06T 2207/10101 (2013.01); G06T 2207/20084 (2013.01); G06T 2207/30041 (2013.01)

(58) Field of Classification Search
CPC . G06T 2207/10101; G06T 2207/20084; G06T 2207/30041; G06T 2211/441; G06T 2211/456
See application file for complete search history.

(56) References Cited

OTHER PUBLICATIONS

Kishi et al., "Posterior Precortical Vitreous Pocket", Archives of Ophthalmology, Jul. 1990, vol. 108, Issue 7, pp. 979-982.

Takura et al., "En Face Imaging of Posterior Precortical Vitreous Pockets Using Swept-Source Optical Coherence Tomography", Investigative Ophthalmology & Visual Science, May 2015, vol. 56, No. 5, pp. 2898-2900.

Schaal et al., "The Premacular Bursa's Shape Revealed In Vivo by Swept-Source Optical Coherence Tomography", Ophthalmology, May 2014, vol. 121, No. 5, pp. 1020-1028.

Gal-Or et al., "In Vivo Imaging of the Fibrillar Architecture of the Posterior Vitreous and its Relationship to the Premacular Bursa, Cloquet's Canal, Prevascular Vitreous Fissures, and Cisterns", Graefe's Archive for Clinical and Experimental Ophthalmology, Jan. 8, 2019, vol. 257, No. 4, pp. 709-714.

Leong et al., "OOCT En Face Analysis of the Posterior Vitreous Reveals Topographic Relationships among Premacular Bursa, Prevascular Fissures, and Cisterns", Ophthalmology Retina, 2019, vol. 4, No. 1, pp. 84-89.

Tsukahara et al., "Posterior Vitreous Detachment as Observed by Wide-Angle OCT Imaging", Ophthalmology, 2018, vol. 125, No. 9, pp. 1372-1383.

Takahashi et al., "Ultra-Widefield Optical Coherence Tomographic Imaging of Posterior Vitreous in Eyes with High Myopia", American Journal of Ophthalmology, 2019, 29 pages.

Takahashi et al., "Importance of Paravascular Vitreal Adhesions for Development of Myopic Macular Retinoschisis Detected by Ultra-Widefield OCT", Ophthalmology, Jul. 2020, 39 pages.

Mao et al., "Deep Learning Based Noise Reduction Method for Automatic 3D Segmentation of the Anterior of amina Cribrosa in Optical Coherence Tomography Volumetric Scans", Biomedical Optics Express, 2019, vol. 10, Issue 11, pp. 5832-5851.

Zhang et al., "Road Extraction by Deep Residual U-Net", IEEE Geoscience and Remote Sensing Letters, arXiv:1711.10684v1 [cs.CV], Nov. 29, 2017, 5 pages.

Kishi, "Vitreous Anatomy and the Vitreomacular Correlation", Japanese Journal of Ophthalmology, vol. 60, Issue 4, Jul. 2016, 35 pages.

Pang et al., "Association of Prevascular Vitreous Fissures and Cisterns with Vitreous Degeneration as Assessed by Swept Source Optical Coherence Tomography", Retina, Sep. 2015, vol. 35, Issue 9, pp. 1875-1882.

Itakura et al., "Evolution of Vitreomacular Detachment in Healthy Subjects", JAMA Ophthalmology, 2013, vol. 131, No. 10, pp. 1348-1352.

Lee et al., "Building Skeleton Models via 3-D Medial Surface Axis Thinning Algorithms", CVGIP: Graphical Models and Image Processing, vol. 56, Issue 6, Nov. 1994, pp. 462-478.

Taubin, "Curve and surface smoothing without shrinkage." Proceedings of IEEE International Conference on Computer Vision, 1995, 6 pages.

Hogan MJ, Alvarado JA, Weddell JE. The Vitreous. In: Hogan MJ, Alvarado JA, Weddell JE, eds. Histology of the Human Eye. Philadelphia: W.B.Saunders, 1971, 32 pages.

Worst JG. Cisternal systems of the fully developed vitreous body in the young adult. Trans Ophthalmol Soc U K 1977;97(4):550-4. (After a diligent effort, a copy of this reference was not found.).

* cited by examiner

APPARATUS AND METHOD FOR IMAGING STRUCTURE IN A TRANSPARENT MEDIUM

CROSS-REFERENCE TO RELATED APPLICATIONS

This application is a non-provisional application of and claims priority to U.S. Provisional Application 63/168,927, filed on Mar. 31, 2021, the entire disclosures of each are incorporated herein by reference.

FIELD OF THE INVENTION

The present disclosure relates generally to imaging structure within a transparent medium such as an eye, and in particular to quantifying and evaluating a structure within gelatinous tissue of an eye for monitoring, evaluating, and/or diagnosing a medical condition.

BACKGROUND OF INVENTION

The eye includes various structures. However, it may be difficult to view those structures in vivo using conventional methods.

SUMMARY OF INVENTION

According to an embodiment of the invention, a medical diagnostic apparatus includes a receiver circuit that receives three-dimensional data of an eye; processing circuitry configured to segment the three-dimensional data into regions that include a target structural element and regions that do not include the target structural element to produce a segmented three-dimensional data set, the segmenting being performed using a plurality of segmentation algorithms, each of the plurality of segmentation algorithms having been trained separately on different two-dimensional data extracted from the three-dimensional data; the processing circuitry further configured to generate at least one metric from the segmented three-dimensional data set; and the processing circuitry is further configured to evaluate a medical condition based on the at least one metric.

In the medical diagnostic apparatus, each segmentation algorithm may correspond to a training plane, and each segmentation algorithm may be trained using data corresponding to a plurality of two-dimensional image slices each parallel to the corresponding training plane.

In the medical diagnostic apparatus, the processing circuitry may include an axial segmentation algorithm corresponding to an axial plane of the eye, a coronal segmentation algorithm corresponding to a coronal plane of the eye, and a sagittal segmentation algorithm corresponding to a sagittal plane of the eye.

In the medical diagnostic apparatus, the segmentation algorithm may produce weights that are used by a neural network to produce a per plane segmented data set from all two dimensional slices parallel to the corresponding training plane in the three-dimensional data and the per plane segmented data set from each segmentation algorithm may be combined by averaging or voting a result at each location in the eye to produce the segmented three-dimensional data set.

In the medical diagnostic apparatus, the segmentation algorithm may produce procedural parameters that are used by the processing circuitry to produce a per plane segmented data set from all two dimensional slices parallel to the corresponding training plane in the three-dimensional data; and the per plane segmented data set from each segmentation algorithm may be combined by averaging or voting a result at each location in the eye to produce the segmented three-dimensional data set.

In the medical diagnostic apparatus, the two-dimensional data may be used to train each of the plurality of segmentation algorithms includes a subset of two dimensional slices taken from the three-dimensional data parallel to a corresponding plane and for which segmentation results are assigned to each coordinate, and the two-dimensional data used to train each of the plurality of segmentation algorithms may further include two dimensional slices corresponding to locations adjacent to slices in the subset of all the two dimensional slices taken from the three-dimensional data parallel to a corresponding plane and for which segmentation results are assigned to each coordinate.

In the medical diagnostic apparatus, the processing circuitry may be further configured to perform the segmentation using the plurality of segmentation algorithms, each of the plurality of segmentation algorithms having been trained separately on different two-dimensional data extracted from the three-dimensional data and from additional three-dimensional data corresponding to one or more eyes other than the eye.

In the medical diagnostic apparatus, the processing circuitry may be configured to generate a skeleton corresponding to the segmented three-dimensional data set, and to generate the at least one metric based on a characteristic of the skeleton.

In the medical diagnostic apparatus, the medical condition may include at least one of congenital vitreoretinal abnormality, vitreoretinal degenerative disease, diabetic retinopathy, myopia, pathologic myopia, age-related macular degeneration, intraocular inflammation and malignancy, glaucoma, and myopic neuropathy.

In the medical diagnostic apparatus, the target structural element may include at least one of a vitreous pocket, a lamina cribosa, and an optic disc.

A medical diagnostic method according to an embodiment of the invention may include receiving three-dimensional data of an eye; segmenting the three-dimensional data into regions that include a target structural element and regions that do not include the target structural element to produce a segmented three-dimensional data set, the segmenting being performed using a plurality of segmentation algorithms, each of the plurality of segmentation algorithms having been trained separately on different two-dimensional data extracted from the three-dimensional data; generating at least one metric from the segmented three-dimensional data set; and evaluating a medical condition based on the at least one metric.

In the medical diagnostic method, each segmentation algorithm may correspond to a training plane, and each segmentation algorithm is trained using data corresponding to a plurality of two-dimensional image slices each parallel to the corresponding training plane.

In the medical diagnostic method, the segmenting may be performed using an axial segmentation algorithm corresponding to an axial plane of the eye, a coronal segmentation algorithm corresponding to a coronal plane of the eye, and a sagittal segmentation algorithm corresponding to a sagittal plane of the eye.

In the medical diagnostic method, the segmentation algorithm may produce weights that are used by a neural network to produce a per plane segmented data set from all two dimensional slices parallel to the corresponding training plane in the three-dimensional data; and the per plane segmented data set from each segmentation algorithm is combined by averaging or voting a result at each location in the eye to produce the segmented three-dimensional data set.

In the medical diagnostic method, the segmentation algorithm may produce procedural parameters that are used to produce a per plane segmented data set from all two dimensional slices parallel to the corresponding training plane in the three-dimensional data; and the per plane segmented data set from each segmentation algorithm is combined by averaging or voting a result at each location in the eye to produce the segmented three-dimensional data set.

In the medical diagnostic method, the two-dimensional data may be used to train each of the plurality of segmentation algorithms includes a subset of two dimensional slices taken from the three-dimensional data parallel to a corresponding plane and for which segmentation results are assigned to each coordinate, and the two-dimensional data used to train each of the plurality of segmentation algorithms further includes two dimensional slices corresponding to locations adjacent to slices in the subset of all the two dimensional slices taken from the three-dimensional data parallel to a corresponding plane and for which segmentation results are assigned to each coordinate.

In the medical diagnostic method, the segmenting may performed using the plurality of segmentation algorithms, each of the plurality of segmentation algorithms having been trained separately on different two-dimensional data extracted from the three-dimensional data and from additional three-dimensional data corresponding to one or more eyes other than the eye.

The medical diagnostic method may further included generating a skeleton corresponding to the segmented three-dimensional data set; and generating the at least one metric based on a characteristic of the skeleton, wherein the medical condition includes at least one of congenital vitreoretinal abnormality, vitreoretinal degenerative disease, diabetic retinopathy, myopia, pathologic myopia, age-related macular degeneration, intraocular inflammation and malignancy, glaucoma, and myopic neuropathy.

In the medical diagnostic method, the target structural element may include at least one of a vitreous pocket, a lamina cribosa, and an optic disc.

A non-transitory computer readable medium storing computer executable instructions, which, when executed by a computer, performs a medical diagnostic method according to an embodiment of the invention that includes receiving three-dimensional data of an eye; segmenting the three-dimensional data into regions that include a target structural element and regions that do not include the target structural element to produce a segmented three-dimensional data set, the segmenting being performed using a plurality of segmentation algorithms, each of the plurality of segmentation algorithms having been trained separately on different two-dimensional data extracted from the three-dimensional data; generating at least one metric from the segmented three-dimensional data set, and evaluating a medical condition based on the at least one metric.

BRIEF DESCRIPTION OF THE DRAWINGS

The scope of the present disclosure is best understood from the following detailed description of exemplary embodiments when read in conjunction with the accompanying drawings, wherein.

DETAILED DESCRIPTION

An eye includes various structures including a vitreous, lamina cribosa, and optic disc. Changes in the optic disc can be signs of glaucoma or myopic neuropathy development.

For example, vitreous is a transparent gel-like structure that makes up about 80% of the eye volume. Because the vitreous is a large, transparent, and moving mass, it is conventionally difficult to view the structure of the vitreous, especially in vivo. Vitreous observations have been mainly obtained by in vitro examinations, for example, by injecting Indian Ink into the vitreous to reveal many ink-filled spaces, called cisterns.

In vivo imaging has been performed using swept-source optical coherence tomography (SS-OCT) horizontal B scan images, which have revealed a posterior precortical vitreous pocket (PPVP) forming a boat-shaped space anterior to the posterior pole of the eye, as well as other fluid-filled spaces in the vitreous (e.g., Cloquet's canal and other cisterns).

Embodiments of the present invention may provide improved imaging and analysis of those structures. Although the following detailed discussion may discuss how the embodiment may be used to image and evaluate the structure of the vitreous, the invention is also equally applicable to any other eye structure, including, for example, the optic disc structure.

OCT B scan images record a two dimensional slice of the vitreous at one specific time and at one fixed position (e.g., at the fovea). However, the vitreous is a gelatinous tissue that moves in whole and in part by eye and body movements, which makes it difficult to interpret a static image of such a dynamic structure. Further, the structure of the vitreous may change immediately, due to the movement, and may also change over time. Similarly, other structural elements in the eye may be difficult to image in vivo. An embodiment of the invention provides a real-time 3D view of the vitreous and/or other eye structural elements allowing better visualization and evaluation of the dynamic vitreous and any changes it may undergo.

Additionally, evidence suggests that the structure of the vitreous, and in particular, vitreous pocket profiles, is an indicator of the aging process in healthy eyes, and could also be an early predictor of eye diseases such as diabetic retinopathy and high myopia.

Figure 1:
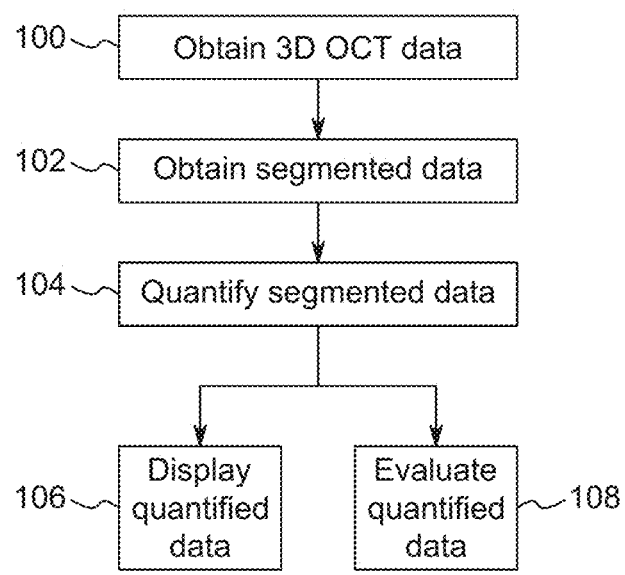
FIG. 1 is a diagram of a method and apparatus for imaging a structure of the vitreous according to an embodiment of the invention.

FIG. 1 shows a flow diagram of an embodiment of a method of imaging structural elements of interest (i.e., target structural elements) in the eye, such as a structure of the vitreous, according to the present invention. 3D OCT data of the subject eye is obtained in step 100, for example, by receiving the data from an OCT scanner, or by performing an OCT scan using an OCT scanner. In step 102, the 3D OCT data is segmented. In step 104, the segmented data is quantified. In step 106 the quantified data is displayed, or in step 108 the quantified data is evaluated, for example, to monitor progress of a medical condition or to compare with a normative database for abnormality detection. The method of FIG. 1 may be performed on one more general purpose computers that are programmed to perform the noted functions. Although FIG. 1, and other diagrams below, are referred to as method flow diagrams, they each also represent a corresponding structural diagram of an apparatus to perform the corresponding functions. As discussed in greater detail below, each of the corresponding functions may be implemented using dedicated circuitry and/or programmable circuitry.

Figure 2:
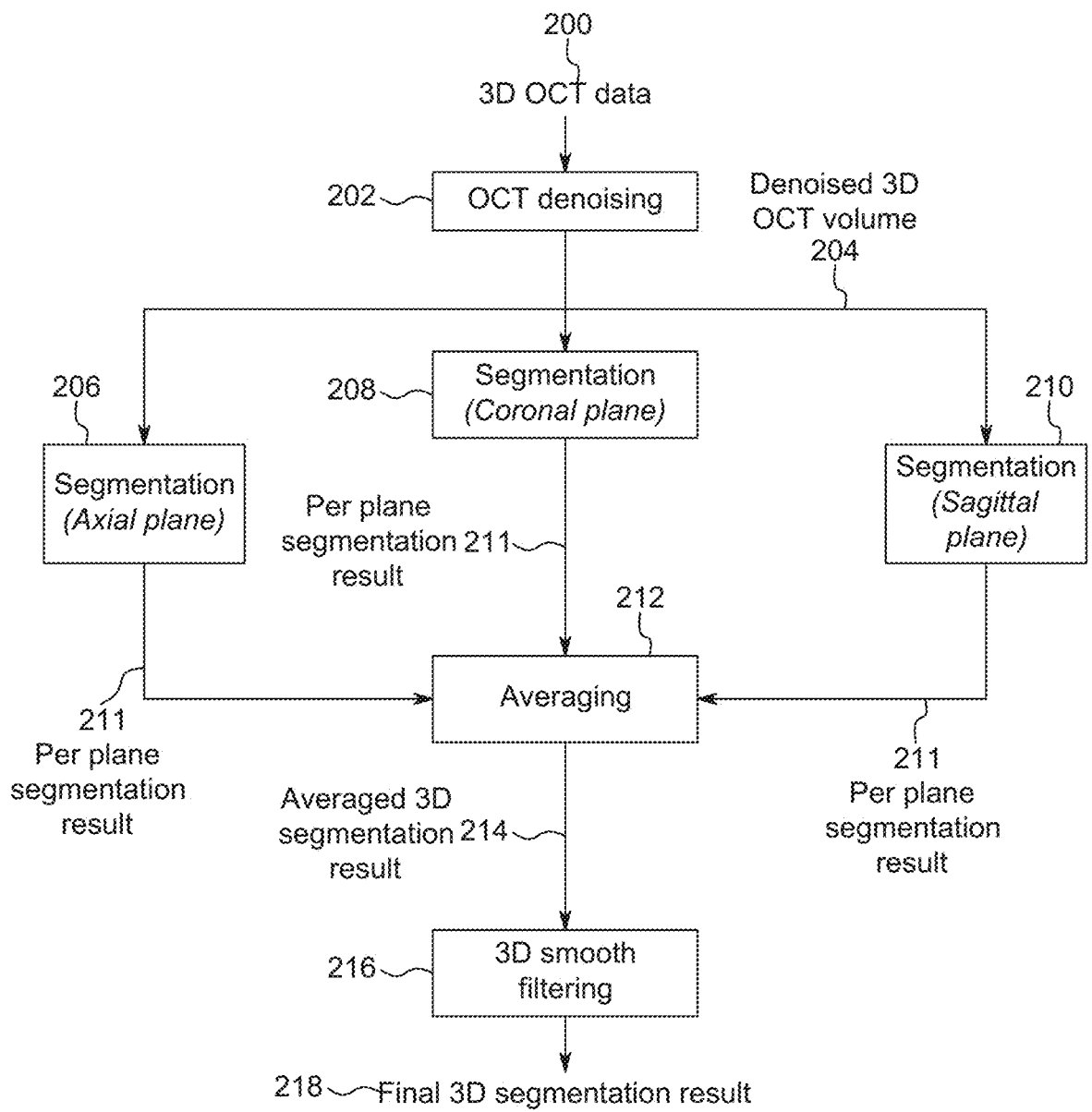
FIG. 2 is a diagram of a method and apparatus for obtaining segmented data from the 3D OCT data according to an embodiment of the invention.

FIG. 2 shows a flow diagram of a method of obtaining segmented data from the 3D OCT data, as in step 102 of FIG. 1. In step 202, the obtained 3D OCT data (i.e., volumetric data) 200 is denoised to improve the signal-to-noise ratio. The embodiment may include an Artificial Intelligence (AI) OCT denoising technique, or other known denoising techniques. The denoising in step 202 produces a denoised 3D OCT volume 204.

The denoised 3D OCT volume 204 is segmented separately in one or more different planes. In the example of FIG. 2, the denoised 3D OCT volume 204 is separately segmented in 3 different planes; thus, segmentation is performed in the axial plane 206, the coronal plane 208, and the sagittal plane 210 of a subject's eye. However, embodiments of the invention include performing the segmentation in other possible planes, for example, with respect to different frames of reference, and in other possible numbers of planes, for example in one or two planes or four or more planes. For each plane, individual OCT images along that plane are selected from the denoised 3D OCT volume 204, and structural elements of interest, such as vitreous pockets, in each OCT image are automatically segmented (i.e., labeled, or otherwise identified). Then, the segmented structural elements, such as the vitreous pockets, from each image are combined to produce a 3D segmentation result for the corresponding plane 211. The segmentation result for each plane 211 indicates the presence or absence of the structural element of interest (e.g., a vitreous pocket) at each location within the imaged volume.

In step 212, the segmentations result of each plane are averaged together, or the results are voted in each location, with the most votes at each location being set as the result for that location. For example, each segmentation result has a binary indication of the presence or absence of the structural element of interest (e.g., a vitreous pocket) at a location (e.g., value of 1 at a location indicating presence of the structural element of interest, and a value of 0 at a location indicating the absence of the structural element of interest). In the averaging step, an average value is calculated for the value of each location from the segmented result in each separate plane (e.g., as calculated in the axial, coronal, and sagittal planes). Then, the averaged value is compared to a threshold value, and comparison results that exceed the threshold value are set to indicate the presence of the structural element of interest in the averaged 3D segmentation result 214. For an average of three planes, as in this example, the threshold value is set to ⅔. However, other threshold values may be used when different numbers of planes are separately segmented.

In step 216, a 3D smoothing process is performed on the averaged 3D segmentation result 214 to produce a final 3D segmentation result 218. The smoothing process further reduces noise and rough edges. The smoothing may be performed using a 3D median filter of size (9, 9, 9). The filter size may be selected based on the physical nature of the segmentation target. A larger filter size, e.g., (15, 15, 15), tends to generate smooth contours but at the risk of removing detail information, and a small filter size, e.g., (3, 3, 3), preserves most of the details but may generate noisy results. Thus, (9, 9, 9) is a good filter size for imaging the relatively large structures of interest (e.g., large vitreous structures), while (3, 3, 3) is a better filter size for imaging smaller tissue structures, such as pores in the lamina cribosa. Additionally, other non-median filters such as Laplacian and/or Taubin filter can also be applied to achieve 3D smoothing.

Figure 3A:
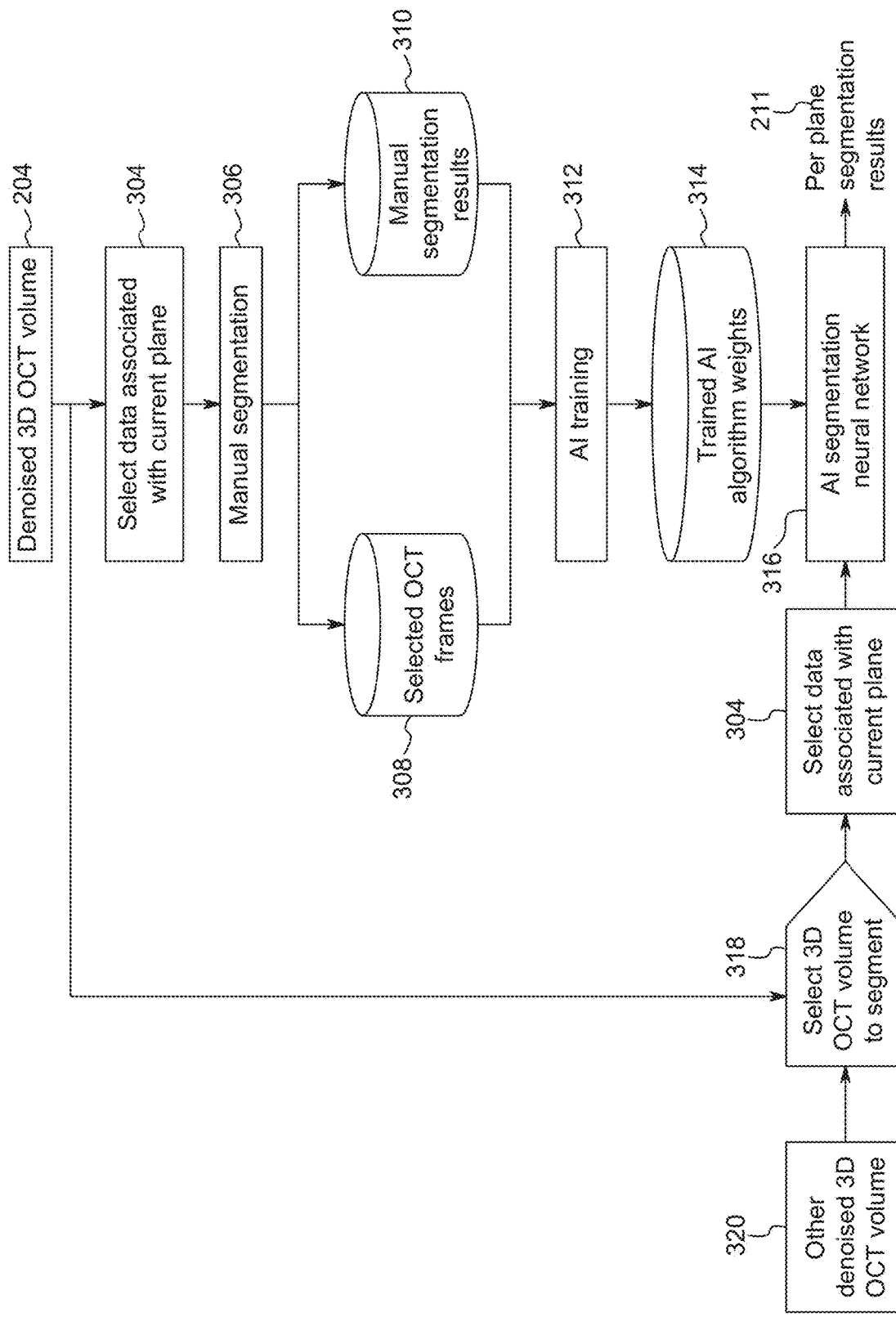
FIG. 3A is a diagram of a method and apparatus for performing per plane segmentation according to an embodiment of the invention.

FIG. 3A shows a detailed flow diagram of the per plane segmentation, such as performed in steps 206, 208, or 210 of FIG. 2. First, to train the AI Algorithm, data associated with the current plane is selected or extracted from the denoised 3D OCT Volume 204 in step 304. For example, data corresponding to a plurality of 2D images, each representing an image plane parallel to the current plane, are selected or extracted from the denoised 3D OCT volume 204 in step 304. Next, representative images are selected from the plurality of 2D images for manual segmentation along the corresponding plane in step 306. For example, the selected images may be one image selected randomly out of a predetermined number of the plurality of 2D images. For example, in step 306, one image may be selected randomly or sequentially from every ten captured images extracted or selected in step 304. Also, in step 306, assignment information for manual segmentation is obtained. For example, in step 306, a manual indication is received indicating whether or not a location includes a structural element of interest (e.g., a vitreous pocket). The manual indication may be generated by a user interface device (e.g., mouse, keyboard, touchscreen, etc.) operated by a human who manual identifies segmentation information in a selected frame. The manual indication and the corresponding location information together form the manual segmentation results 310. The output of the manual segmentation step 306 includes the selected OCT frames 308 (i.e., the data corresponding to the 2D images on which the manual segmentation was performed) and the manual segmentation results 310 (i.e., the information indicating where the structural elements of interest are located).

Figure 3B:
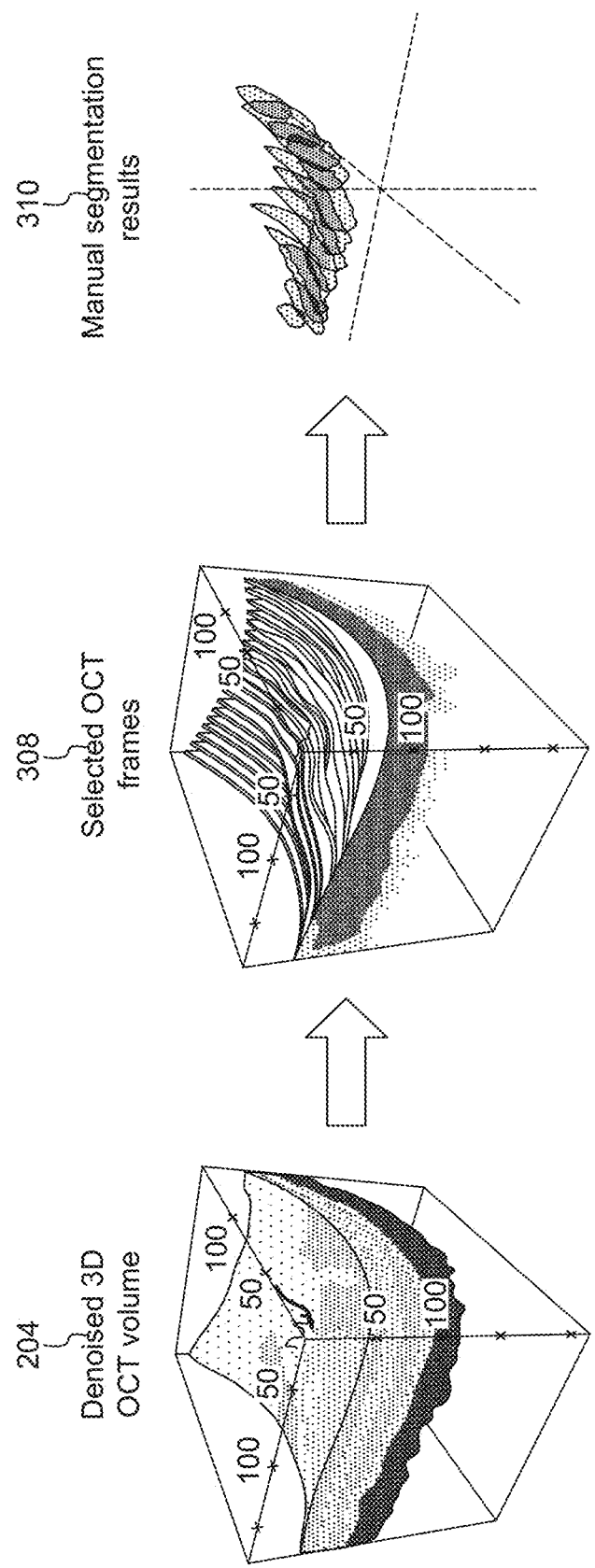
FIG. 3B is a graphical example of a denoised 3D OCT volume according to an embodiment of the invention.

FIG. 3B shows a graphical example of a denoised 3D OCT volume 204 produced by step 304, selected OCT frames 308 produced by step 306, and manual segmentation results 310 also produced by step 306.

In step 312, an AI algorithm is trained using the selected OCT frames 308 and the manual segmentation results 310. The selected OCT frames 308 are used as input data for the training, and the manual segmentation results are used as ground truth data. The AI algorithm may be implemented using a neural network or other machine learning algorithms such as the support vector machine. For example, a deep residual neural network may be used to perform the AI algorithm. During training, weights between the nodes in a neural network or parameters in a procedural algorithm (collectively referred to herein as "weights") in an AI algorithm are gradually adjusted by the training process such that the AI algorithm is trained to generate an output image based on the input image that best matches the corresponding ground truth image. This training procedure 312 continues until a termination criterion is met. For example, in one embodiment, training is completed when all of the training data has passed through the AI algorithm a predetermined number of times (e.g., 100 times). In other embodiments, training is completed when the output result of a test image stops changing by a predetermined factor. The result of the AI training process 312 are the trained AI algorithm weights 314.

Once training is complete, the trained AI Algorithm weights 314 may be used by the AI segmentation neural network 316 to perform structural element of interest segmentation (e.g., vitreous pocket segmentation) automatically on 2D image slices other than those used to perform the training. For example, all images parallel to the current plane 304 in the denoised 3D OCT volume 204 can be processed by the AI segmentation neural network 316 using the trained AI algorithm weights 314 to produce per plane segmentation results 211. These results will include structural element segmentation identification (i.e., identification of whether or not each coordinate in each slice includes the structural element of interest) performed on each image slide of data associated with the current plane from the denoised 3D OCT volume 304 (not just the manually segmented image slices).

Alternatively, as selected by step 318, instead of using the denoised 3D OCT volume 204 from which the training data was extracted/selected, a different denoised 3D OCT volume 320 may be segmented by the AI segmentation 316 using the trained AI algorithm weights 314. The other denoised 3D OCT volume 320 may be data corresponding to the same eye for which the denoised 3D OCT volume 204 was obtained, however, at a different (later or earlier) date or time. Alternatively, the other denoised 3D OCT volume 320 may be data corresponding to another eye of the same person from whom the denoised 3D OCT volume 204 was obtained. Also, the other denoised 3D OCT volume 320 may be data corresponding to an eye of a different person than the person from whom the denoised 3D OCT volume 204 was obtained.

If the AI algorithm is trained using data from a single subject's eye, the algorithm can perform well for other images (that were not manually segmented) from the subject. To use the trained AI algorithm successfully to segment images from other subjects, it is advantageous to include training images from many subjects. In other words, if the trained AI algorithm is trained using images from only one subject eye, the trained AI algorithm becomes specialized for that one subject eye (or possibly both eyes of the subject) but may not be useful for the eyes of other subjects. Vice versa, the AI algorithm can be trained to achieve high generalizability using a large variation of subject eye data (i.e., data from many subject eyes) but may not achieve the same accuracy for a specific subject in comparison with the specialized algorithm. Therefore, depending on the final goal (e.g., accuracy vs. automation) and available training data, different training approaches can be applied. For example, when there is a limited amount of available manually annotated images (i.e., images annotated to identify the structural elements of interest, such as vitreous pockets), it is advantageous to train the AI algorithm per subject per eye to maximize accuracy.

By training the AI algorithm using 1 manually segmented frame out of every N frames, the trained AI algorithm weights 314 can subsequently be used to automatically perform segmentation on all the frames (i.e., the N−1 frames) that were not manually segmented. The output of the AI segmentation 316 is a set of images from the corresponding plane containing the segmentation results.

In the above descriptions, the training input image consists of randomly selected and isolated 2D images in the corresponding plane. However, according to a further embodiment, accuracy of the AI algorithm can be improved in step 308 by providing not only the selected frames 308 for which the manual segmentation results have been set 310, but also, including within the selected frames 308 and providing to the AI training 312, additional adjacent frames, which are frames corresponding to regions that are physically adjacent to the randomly or sequentially selected frames for which the manual segmentation results have been set. Inventors have found that providing the additional information regarding adjacent image slices as part of the AI Training 312 improves the training process.

Figure 3C:
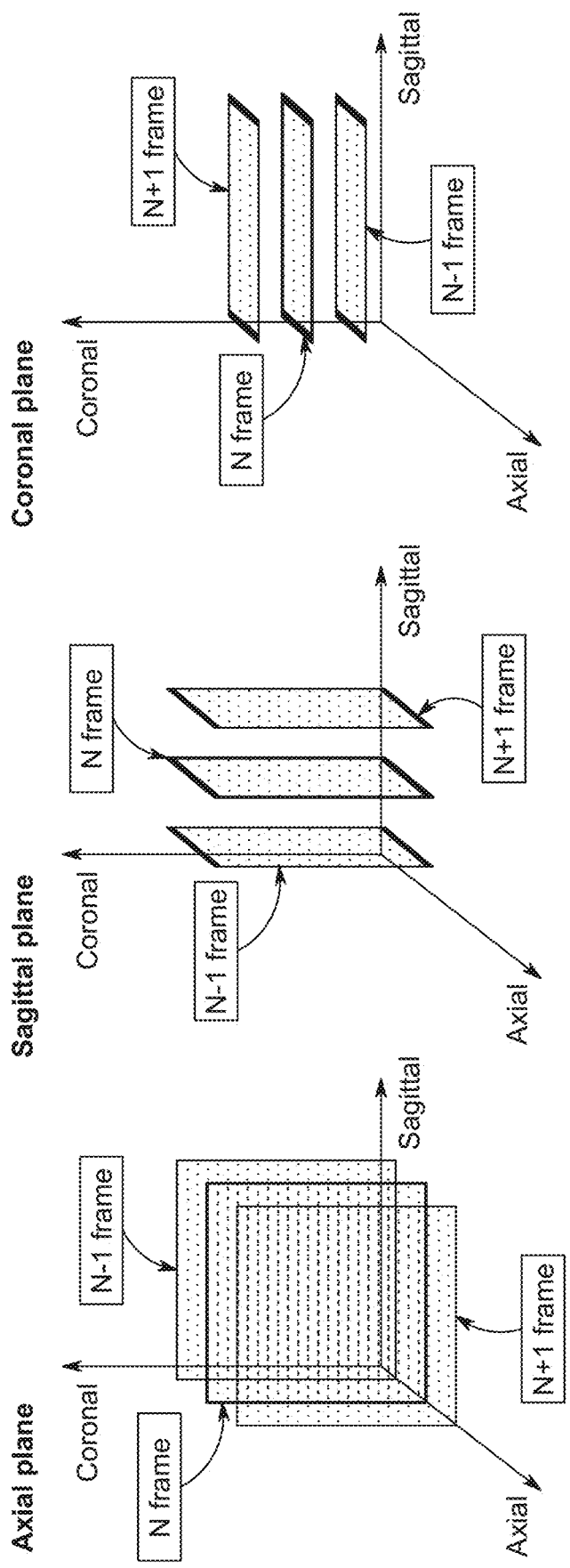
FIG. 3C is an example showing physically adjacent frames to a frame for which manual segmentation is performed according to an embodiment of the invention.

FIG. 3C shows an example of physically adjacent frames N−1, N, and N+1 within corresponding axial, sagittal, and coronal planes. In this example, the manual segmentation results are only available for the N-th frame. During training, N−1, N, and N+1 frames are combined to create a 3D image (with three channels) as input, while manual segmentation for the N-th frame is set as the target. The signal-to-noise ratio of the imaged vitreous pockets may become higher using this approach because adding information from neighboring frames to the training data helps to reduce the noise and improve the visibility of the vitreous pocket.

Figure 4:
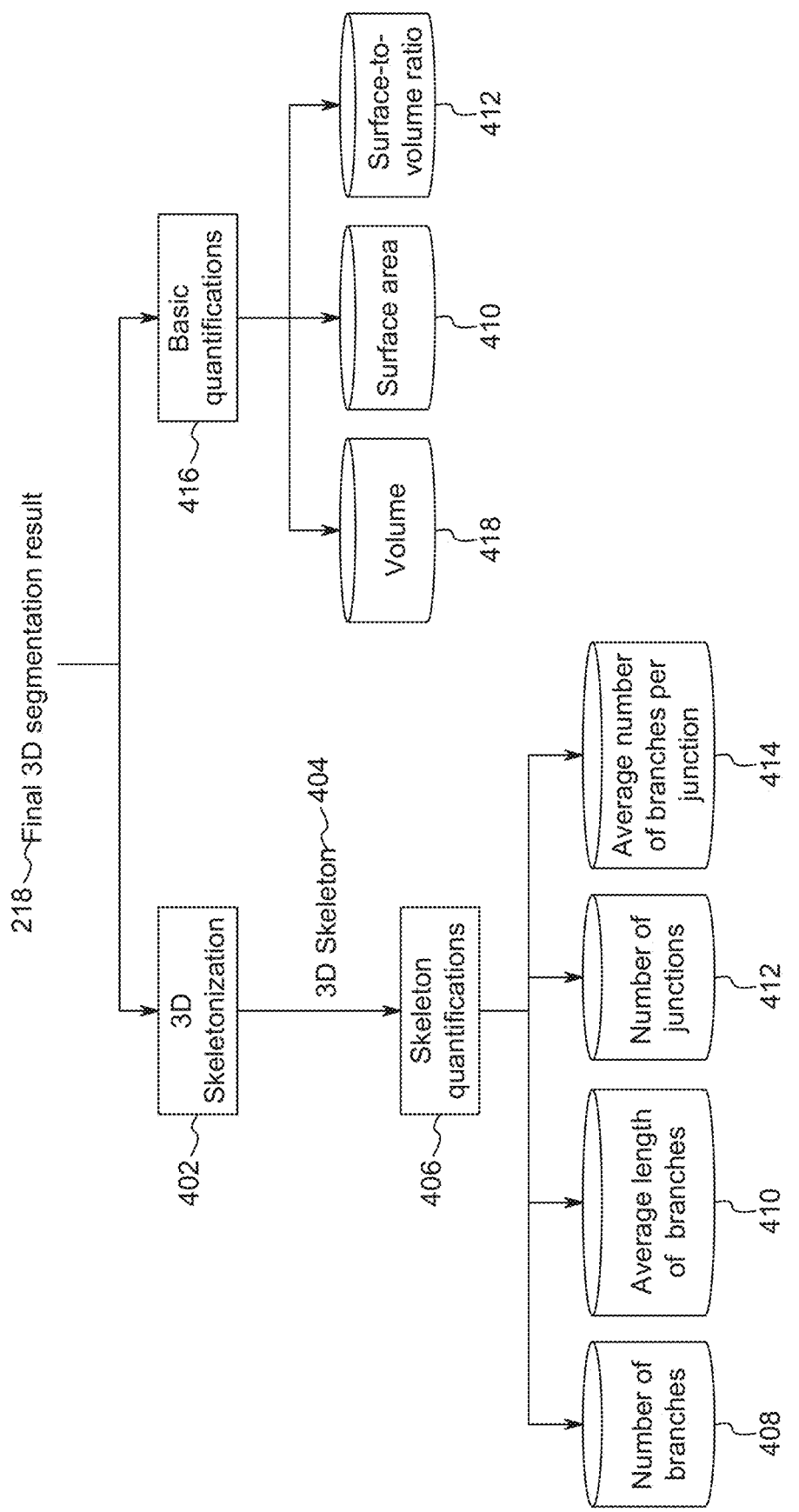
FIG. 4 is a diagram of a method and apparatus for performing a segmented data step according to an embodiment of the invention.

FIG. 4 shows a detailed flow diagram of the quantify segmented data step 104 in FIG. 1. The final segmentation result 218 is quantified to produce various metrics that are in turn used for monitoring, evaluating, and diagnosing medical conditions. In step 402 the final segmentation result 218 undergoes 3D skeletonization 402 to produce a 3D skeleton 304 of the structural elements of interest (e.g., vitreous pockets) from which a skeleton quantification process 406 may extract skeleton characteristics including: number of branches 408, average length of branches 410, number of junctions 412, average number of branches per junction 414. Further basic quantification process 416 may extract metrics for the structural elements of interest from the final 3D segmentation result 218, such as: volume 418, surface area 310, and surface-to-volume ratio 412.

Figure 5A:
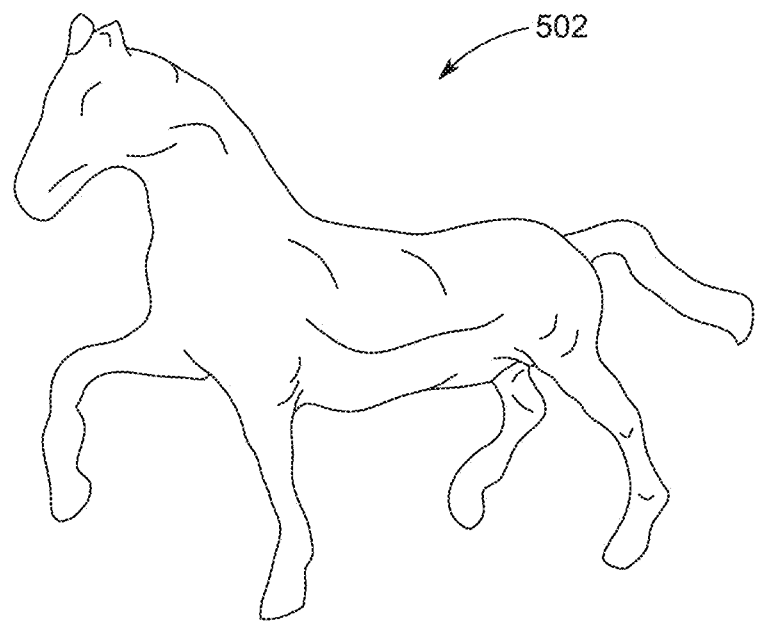
FIG. 5A is an example of a 3D object from which a skeletonized view may be produced.
Figure 5B:
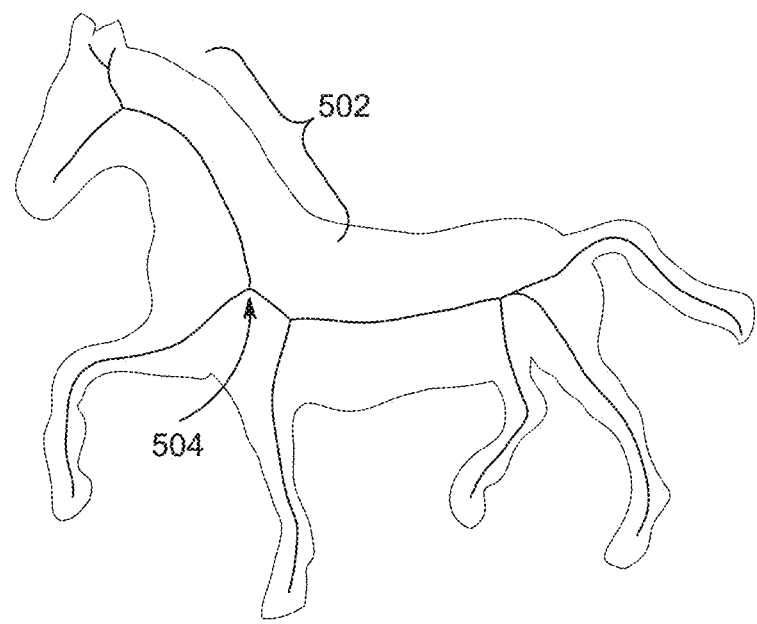
FIG. 5B is an example of a skeletonized view produced from the object in FIG. 5A according to an embodiment of the invention.

FIGS. 5A and 5B show an example of skeletonization, which is a method to quantify the shape of a 3D object. FIG. 5A represents an image of a 3D object 502 (i.e., a horse). FIG. 5B shows a skeletonized view of the horse produced by 3D skeletonization 402. The skeletonized view includes an arrangement of branches 502 connected at junctions 504. For example, the 3D skeletonization 402 may include a process of thinning a 3D object to a set of points that is equidistant to the surface of the 3D object. Together with the distance of each point to the object's surface, the resulting 3D skeleton can serve as a representation of the shape of the 3D object from which additional measurements and metrics may be extracted. The complexity of a 3D object may be characterized by the number of branches, a simpler 3D object tends to have fewer number of branches. The sphere-likeness is characterized by the number of branches per junction with a perfect sphere having only one junction and no branches.

Other metrics can also be extracted from the final 3D segmentation result 218, including: height of the structural element of interest (e.g., a vitreous pocket); width of the structural element of interest along the superior-inferior direction; width of the structural element of interest along the nasal-temporal direction, and the spatial relationship between each space (i.e., the presence or absence of a connection between each space).

These metrics (aka, structural element of interest profiles) taken individually or in combinations and sub-combinations represent an indicator of the aging process in healthy eyes. For example, metrics for a vitreous pocket are also an early predictor of eye diseases such as congenital vitreoretinal abnormality (persistent hyperplastic primary vitreous, persistent hyaloid artery, retinopathy of prematurity, etc), vitreoretinal degenerative disease (familial exudative vitreoretinopathy, enhanced Scone syndrome, etc), diabetic retinopathy (from subclinical phase to advanced disease), myopia and pathologic myopia, age-related macular degeneration, and intraocular inflammation and malignancy (uveitis, intraocular lymphoma, etc). For example, the vitreous pocket formation may predate pathological myopia and therefore could be used as an early sign for pathological myopia detection. Optic disc structures could be used monitor and manage patients with glaucoma and myopic neuropathy.

Without the need for special protocols, the techniques used here do not need to be connected directly or simultaneously to an OCT scanner and can be applied retrospectively on any existing 3D data.

As used herein, an element or step recited in the singular and proceeded with the word "a" or "an" should be understood as not excluding plural elements or steps, unless such exclusion is explicitly recited. Furthermore, references to "one embodiment" of the present invention are not intended to be interpreted as excluding the existence of additional embodiments that also incorporate the recited features.

Control and processing methods and/or systems described herein may be implemented using computer programming or engineering techniques including computer software, firmware, hardware or any combination or subset thereof, wherein the technical effects may include at least processing of the three-dimensional data and diagnostic metrics according to the present disclosure.

Figure 6:
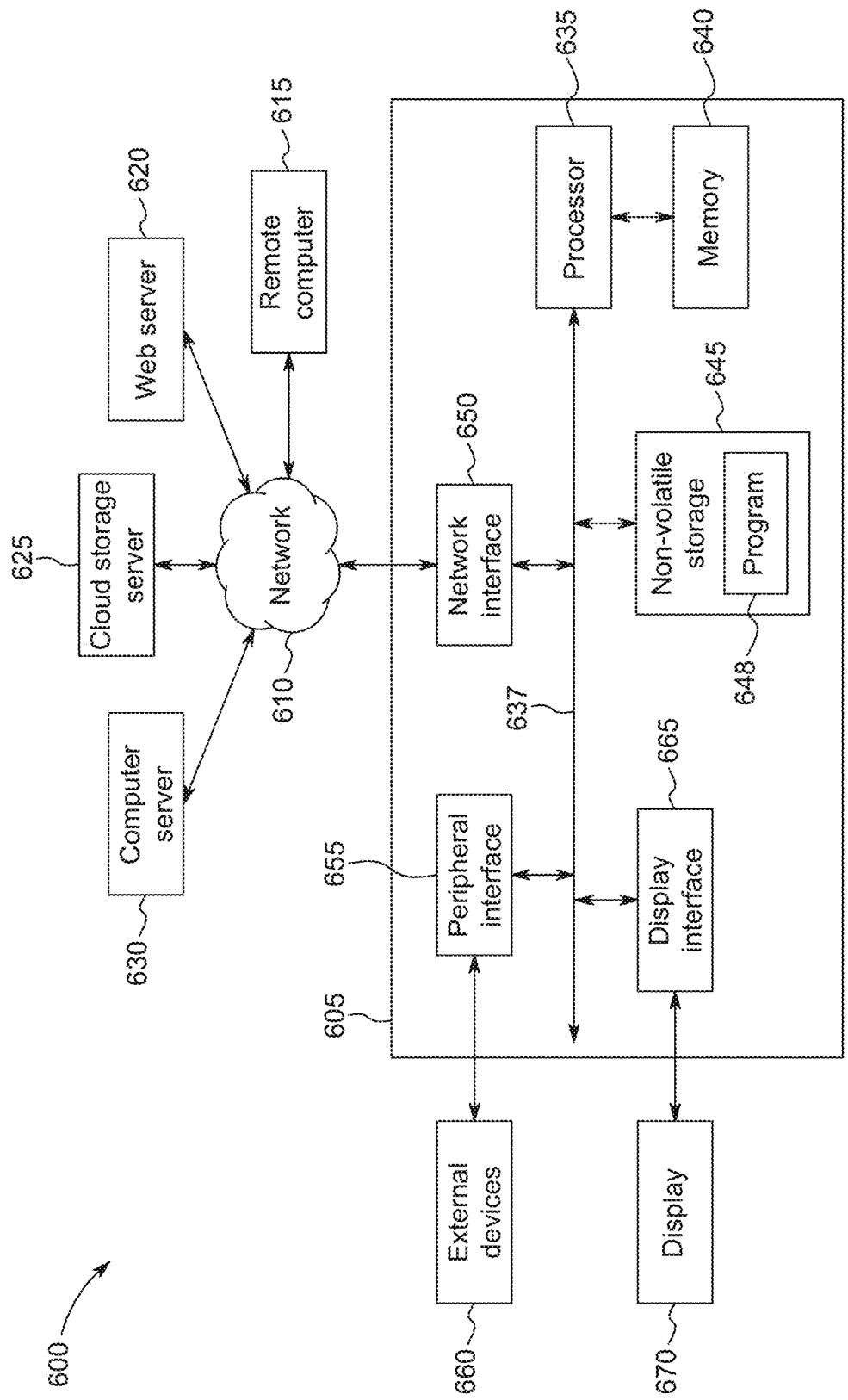
FIG. 6 is an example of an apparatus configuration according to an embodiment of the invention.

FIG. 6 illustrates a block diagram of a computer that may implement the various embodiments described herein. Control and processing aspects of the present disclosure may be embodied as a system, a method, and/or a computer program product. The computer program product may include a computer readable storage medium on which computer readable program instructions are recorded that may cause one or more processors to carry out aspects of the embodiment.

The computer readable storage medium may be a tangible and non-transitory device that can store instructions for use by an instruction execution device (processor). The computer readable storage medium may be, for example, but is not limited to, an electronic storage device, a magnetic storage device, an optical storage device, an electromagnetic storage device, a semiconductor storage device, or any appropriate combination of these devices. A non-exhaustive list of more specific examples of the computer readable storage medium includes each of the following (and appropriate combinations): flexible disk, hard disk, solid-state drive (SSD), random access memory (RAM), read-only memory (ROM), erasable programmable read-only memory (EPROM or Flash), static random access memory (SRAM), compact disc (CD or CD-ROM), digital versatile disk (DVD), MO, and memory card or stick. A computer readable storage medium, as used in this disclosure, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions implementing the functions described in this disclosure can be downloaded to an appropriate computing or processing device from a computer readable storage medium or to an external computer or external storage device via a global network (i.e., the Internet), a local area network, a wide area network and/or a wireless network. The network may include copper transmission wires, optical communication fibers, wireless transmission, routers, firewalls, switches, gateway computers and/or edge servers. A network adapter card or network interface in each computing or processing device may receive computer readable program instructions from the network and forward the computer readable program instructions for storage in a computer readable storage medium within the computing or processing device.

Computer readable program instructions for carrying out operations of the present disclosure may include machine language instructions and/or microcode, which may be compiled or interpreted from source code written in any combination of one or more programming languages, including assembly language, Basic, Fortran, Java, Python, R, C, C++, C# or similar programming languages. The computer readable program instructions may execute entirely on a user's personal computer, notebook computer, tablet, or smartphone, entirely on a remote computer or computer server, or any combination of these computing devices. The remote computer or computer server may be connected to the user's device or devices through a computer network, including a local area network or a wide area network, or a global network (i.e., the Internet). In some embodiments, electronic circuitry including, for example, programmable logic circuitry, field-programmable gate arrays (FPGA), or programmable logic arrays (PLA) may execute the computer readable program instructions by using information from the computer readable program instructions to configure or customize the electronic circuitry, in order to perform aspects of the present disclosure.

Aspects of the present disclosure are described herein with reference to flow diagrams and block diagrams of methods, apparatus (systems), and computer program products according to embodiments of the disclosure. It will be understood by those skilled in the art that each block of the flow diagrams and block diagrams, and combinations of blocks in the flow diagrams and block diagrams, can be implemented by computer readable program instructions.

The computer readable program instructions that may implement the systems and methods described in this disclosure may be provided to one or more processors (and/or one or more cores within a processor) of a general purpose computer, special purpose computer, or other programmable apparatus to produce a machine, such that the instructions, which execute via the processor of the computer or other programmable apparatus, create a system for implementing the functions specified in the flow diagrams and block diagrams in the present disclosure. These computer readable program instructions may also be stored in a computer readable storage medium that can direct a computer, a programmable apparatus, and/or other devices to function in a particular manner, such that the computer readable storage medium having stored instructions is an article of manufacture including instructions which implement aspects of the functions specified in the flow diagrams and block diagrams in the present disclosure.

The computer readable program instructions may also be loaded onto a computer, other programmable apparatus, or other device to cause a series of operational steps to be performed on the computer, other programmable apparatus or other device to produce a computer implemented process, such that the instructions which execute on the computer, other programmable apparatus, or other device implement the functions specified in the flow diagrams and block diagrams in the present disclosure.

FIG. 6 is a functional block diagram illustrating a networked system 600 of one or more networked computers and servers. In an embodiment, the hardware and software environment illustrated in FIG. 6 may provide an exemplary platform for implementation of the software and/or methods according to the present disclosure. Referring to FIG. 6, a networked system 600 may include, but is not limited to, computer 605, network 610, remote computer 615, web server 620, cloud storage server 625 and computer server 630. In some embodiments, multiple instances of one or more of the functional blocks illustrated in FIG. 6 may be employed.

Additional detail of a computer 605 is also shown in FIG. 6. The functional blocks illustrated within computer 605 are provided only to establish exemplary functionality and are not intended to be exhaustive. And while details are not provided for remote computer 615, web server 620, cloud storage server 625 and computer server 630, these other computers and devices may include similar functionality to that shown for computer 605. Computer 605 may be a personal computer (PC), a desktop computer, laptop computer, tablet computer, netbook computer, a personal digital assistant (PDA), a smart phone, or any other programmable electronic device capable of communicating with other devices on network 610.

Computer 605 may include processor 635, bus 637, memory 640, non-volatile storage 645, network interface 650, peripheral interface 655 and display interface 665. Each of these functions may be implemented, in some embodiments, as individual electronic subsystems (integrated circuit chip or combination of chips and associated devices), or, in other embodiments, some combination of functions may be implemented on a single chip (sometimes called a system on chip or SoC).

Processor 635 may be one or more single or multi-chip microprocessors, such as those designed and/or manufactured by Intel Corporation, Advanced Micro Devices, Inc. (AMD), Arm Holdings (Arm), Apple Computer, etc. Examples of microprocessors include Celeron, Pentium, Core i3, Core i5 and Core i7 from Intel Corporation; Opteron, Phenom, Athlon, Turion and Ryzen from AMD; and Cortex-A, Cortex-R and Cortex-M from Arm. Bus 637 may be a proprietary or industry standard high-speed parallel or serial peripheral interconnect bus, such as ISA, PCI, PCI Express (PCI-c), AGP, and the like.

Memory 640 and non-volatile storage 645 may be computer-readable storage media. Memory 640 may include any suitable volatile storage devices such as Dynamic Random Access Memory (DRAM) and Static Random Access Memory (SRAM). Non-volatile storage 645 may include one or more of the following: flexible disk, hard disk, solid-state drive (SSD), read-only memory (ROM), erasable programmable read-only memory (EPROM or Flash), compact disc (CD or CD-ROM), digital versatile disk (DVD) and memory card or stick.

Program 648 may be a collection of machine readable instructions and/or data that is stored in non-volatile storage 645 and is used to create, manage and control certain software functions that are discussed in detail elsewhere in the present disclosure and illustrated in the drawings. In some embodiments, memory 640 may be considerably faster than non-volatile storage 645. In such embodiments, program 648 may be transferred from non-volatile storage 645 to memory 640 prior to execution by processor 635.

Computer 605 may be capable of communicating and interacting with other computers via network 610 through network interface 650. Network 610 may be, for example, a local area network (LAN), a wide area network (WAN) such as the Internet, or a combination of the two, and may include wired, wireless, or fiber optic connections. In general, network 610 can be any combination of connections and protocols that support communications between two or more computers and related devices.

Peripheral interface 655 may allow for input and output of data with other devices that may be connected locally with computer 605. For example, peripheral interface 655 may provide a connection to external devices 660. External devices 660 may include devices such as a keyboard, a mouse, a keypad, a touch screen, and/or other suitable input devices. External devices 660 may also include portable computer-readable storage media such as, for example, thumb drives, portable optical or magnetic disks, and memory cards. Software and data used to practice embodiments of the present disclosure, for example, program 648, may be stored on such portable computer-readable storage media. In such embodiments, software may be loaded onto non-volatile storage 645 or, alternatively, directly into memory 640 via peripheral interface 655. Peripheral interface 655 may use an industry standard connection, such as RS-232 or Universal Serial Bus (USB), to connect with external devices 660.

Display interface 665 may connect computer 605 to display 670. Display 670 may be used, in some embodiments, to present a command line or graphical user interface to a user of computer 605. Display interface 665 may connect to display 670 using one or more proprietary or industry standard connections, such as VGA, DVI, DisplayPort and HDMI.

As described above, network interface 650, provides for communications with other computing and storage systems or devices external to computer 605. Software programs and data discussed herein may be downloaded from, for example, remote computer 615, web server 620, cloud storage server 625 and computer server 630 to non-volatile storage 645 through network interface 650 and network 610. Furthermore, the systems and methods described in this disclosure may be executed by one or more computers connected to computer 605 through network interface 650 and network 610. For example, in some embodiments the systems and methods described in this disclosure may be executed by remote computer 615, computer server 630, or a combination of the interconnected computers on network 610.

Data, datasets and/or databases employed in embodiments of the systems and methods described in this disclosure may be stored and or downloaded from remote computer 615, web server 620, cloud storage server 625 and computer server 630.

Numerous modifications and variations of the present invention are possible in light of the above teachings. It is therefore to be understood that within the scope of the appended claims, the invention may be practiced otherwise than as specifically described herein.

The invention claimed is:

1. A medical diagnostic apparatus, comprising:
a receiver circuit that receives three-dimensional data of an eye;
processing circuitry configured to segment the three-dimensional data into regions that include a target structural element and regions that do not include the target structural element to produce a segmented three-dimensional data set, the segmenting being performed using a plurality of segmentation algorithms, each of the plurality of segmentation algorithms having been trained separately on different two-dimensional data extracted from the three-dimensional data;
the processing circuitry further configured to generate at least one metric from the segmented three-dimensional data set; and
the processing circuitry is further configured to evaluate a medical condition based on the at least one metric.

2. The medical diagnostic apparatus according to claim 1, wherein each segmentation algorithm corresponds to a training plane, and each segmentation algorithm is trained using data corresponding to a plurality of two-dimensional image slices each parallel to the corresponding training plane.

3. The medical diagnostic apparatus according to claim 2, wherein the processing circuitry includes an axial segmentation algorithm corresponding to an axial plane of the eye, a coronal segmentation algorithm corresponding to a coronal plane of the eye, and a sagittal segmentation algorithm corresponding to a sagittal plane of the eye.

4. The medical diagnostic apparatus according to claim 2, wherein:
the segmentation algorithm produces weights that are used by a neural network to produce a per plane segmented data set from all two dimensional slices parallel to the corresponding training plane in the three-dimensional data, and
the per plane segmented data set from each segmentation algorithm is combined by averaging or voting a result at each location in the eye to produce the segmented three-dimensional data set.

5. The medical diagnostic apparatus according to claim 2, wherein:
the segmentation algorithm produces procedural parameters that are used by the processing circuitry to produce a per plane segmented data set from all two dimensional slices parallel to the corresponding training plane in the three-dimensional data; and
the per plane segmented data set from each segmentation algorithm is combined by averaging or voting a result at each location in the eye to produce the segmented three-dimensional data set.

6. The medical diagnostic apparatus according to claim 1, wherein
the two-dimensional data used to train each of the plurality of segmentation algorithms includes a subset of two dimensional slices taken from the three-dimensional data parallel to a corresponding plane and for which segmentation results are assigned to each coordinate, and
the two-dimensional data used to train each of the plurality of segmentation algorithms further includes two dimensional slices corresponding to locations adjacent to slices in the subset of all the two dimensional slices taken from the three-dimensional data parallel to a corresponding plane and for which segmentation results are assigned to each coordinate.

7. The medical diagnostic apparatus according to claim 1, wherein the processing circuitry is further configured to perform the segmentation using the plurality of segmentation algorithms, each of the plurality of segmentation algorithms having been trained separately on different two-dimensional data extracted from the three-dimensional data and from additional three-dimensional data corresponding to one or more eyes other than the eye.

8. The medical diagnostic apparatus according to claim 1, wherein the processing circuitry is configured to generate a skeleton corresponding to the segmented three-dimensional data set, and to generate the at least one metric based on a characteristic of the skeleton.

9. The medical diagnostic apparatus according to claim 1, wherein the medical condition includes at least one of congenital vitreoretinal abnormality, vitreoretinal degenerative disease, diabetic retinopathy, myopia, pathologic myopia, age-related macular degeneration, intraocular inflammation and malignancy, glaucoma, and myopic neuropathy.

10. The medical diagnostic apparatus according to claim 1, wherein the target structural element includes at least one of a vitreous pocket, a lamina cribosa, and an optic disc.

11. A medical diagnostic method comprising:
receiving three-dimensional data of an eye;
segmenting the three-dimensional data into regions that include a target structural element and regions that do not include the target structural element to produce a segmented three-dimensional data set, the segmenting being performed using a plurality of segmentation algorithms, each of the plurality of segmentation algorithms having been trained separately on different two-dimensional data extracted from the three-dimensional data;
generating at least one metric from the segmented three-dimensional data set; and
evaluating a medical condition based on the at least one metric.

12. The medical diagnostic method according to claim 11, wherein each segmentation algorithm corresponds to a training plane, and each segmentation algorithm is trained using data corresponding to a plurality of two-dimensional image slices each parallel to the corresponding training plane.

13. The medical diagnostic method according to claim 12, wherein the segmenting is performed using an axial segmentation algorithm corresponding to an axial plane of the eye, a coronal segmentation algorithm corresponding to a coronal plane of the eye, and a sagittal segmentation algorithm corresponding to a sagittal plane of the eye.

14. The medical diagnostic method according to claim 12, wherein:
the segmentation algorithm produces weights that are used by a neural network to produce a per plane segmented data set from all two dimensional slices parallel to the corresponding training plane in the three-dimensional data; and
the per plane segmented data set from each segmentation algorithm is combined by averaging or voting a result at each location in the eye to produce the segmented three-dimensional data set.

15. The medical diagnostic method according to claim 12, wherein:
the segmentation algorithm produces procedural parameters that are used to produce a per plane segmented data set from all two dimensional slices parallel to the corresponding training plane in the three-dimensional data; and the per plane segmented data set from each segmentation algorithm is combined by averaging or voting a result at each location in the eye to produce the segmented three-dimensional data set.

16. The medical diagnostic method according to claim 11, wherein
the two-dimensional data used to train each of the plurality of segmentation algorithms includes a subset of two dimensional slices taken from the three-dimensional data parallel to a corresponding plane and for which segmentation results are assigned to each coordinate, and
the two-dimensional data used to train each of the plurality of segmentation algorithms further includes two dimensional slices corresponding to locations adjacent to slices in the subset of all the two dimensional slices taken from the three-dimensional data parallel to a corresponding plane and for which segmentation results are assigned to each coordinate.

17. The medical diagnostic method according to claim 11, wherein the segmenting is performed using the plurality of segmentation algorithms, each of the plurality of segmentation algorithms having been trained separately on different two-dimensional data extracted from the three-dimensional data and from additional three-dimensional data corresponding to one or more eyes other than the eye.

18. The medical diagnostic method according to claim 11, further comprising:
generating a skeleton corresponding to the segmented three-dimensional data set; and
generating the at least one metric based on a characteristic of the skeleton,
wherein the medical condition includes at least one of congenital vitreoretinal abnormality, vitreoretinal degenerative disease, diabetic retinopathy, myopia, pathologic myopia, age-related macular degeneration, intraocular inflammation and malignancy, glaucoma, and myopic neuropathy.

19. The medical diagnostic method according to claim 11, wherein the target structural element includes at least one of a vitreous pocket, a lamina cribosa, and an optic disc.

20. A non-transitory computer readable medium storing computer executable instructions, which, when executed by a computer, performs a medical diagnostic method comprising:
receiving three-dimensional data of an eye;
segmenting the three-dimensional data into regions that include a target structural element and regions that do not include the target structural element to produce a segmented three-dimensional data set, the segmenting being performed using a plurality of segmentation algorithms, each of the plurality of segmentation algorithms having been trained separately on different two-dimensional data extracted from the three-dimensional data;
generating at least one metric from the segmented three-dimensional data set; and
evaluating a medical condition based on the at least one metric.

* * * * *